US007511007B2

(12) United States Patent
Tichy et al.

(10) Patent No.: US 7,511,007 B2
(45) Date of Patent: Mar. 31, 2009

(54) AQUEOUS SANITIZERS, DISINFECTANTS, AND/OR STERILANTS WITH LOW PEROXYGEN CONTENT

(75) Inventors: Daryl J. Tichy, Orem, UT (US); Brian G. Larson, Alpine, UT (US)

(73) Assignee: Solutions BioMed, LLC, Orem, UT (US)

( * ) Notice: Subject to any disclaimer, the term of this patent is extended or adjusted under 35 U.S.C. 154(b) by 169 days.

(21) Appl. No.: 11/510,516

(22) Filed: Aug. 24, 2006

(65) Prior Publication Data

US 2007/0053850 A1 Mar. 8, 2007

Related U.S. Application Data

(63) Continuation-in-part of application No. 11/361,836, filed on Feb. 24, 2006, and a continuation-in-part of application No. 11/361,841, filed on Feb. 24, 2006, and a continuation-in-part of application No. 11/361,837, filed on Feb. 24, 2006, and a continuation-in-part of application No. 11/361,665, filed on Feb. 24, 2006, now Pat. No. 7,351,684.

(60) Provisional application No. 60/656,723, filed on Feb. 25, 2005.

(51) Int. Cl.
*C11D 7/18* (2006.01)
*C11D 3/48* (2006.01)

(52) U.S. Cl. ....................... 510/372; 510/161; 510/199; 510/235; 510/238; 510/302; 510/309; 510/319; 510/362; 510/370; 510/367; 510/375; 510/382

(58) Field of Classification Search ................. 510/372, 510/161, 199, 235, 238, 302, 309, 319, 362, 510/370, 367, 375, 382
See application file for complete search history.

(56) References Cited

U.S. PATENT DOCUMENTS

| | | | | |
|---|---|---|---|---|
| 716,077 | A | 12/1902 | Morrin | |
| 734,467 | A | 7/1903 | Martien | |
| 2,103,999 | A | 12/1937 | Muller et al. | |
| 2,304,104 | A | 12/1942 | Klabunde et al. | |
| 4,021,338 | A | 5/1977 | Harkin | |
| 4,297,298 | A | 10/1981 | Crommelynch et al. | |
| 4,311,598 | A | 1/1982 | Verachtert | |
| 4,321,255 | A | 3/1982 | Boden | |
| 4,414,127 | A | 11/1983 | Fu | |
| 4,655,975 | A | 4/1987 | Snoble | |
| 4,826,658 | A | 5/1989 | Kay | |
| 4,915,955 | A | 4/1990 | Gomori | |
| 5,349,083 | A | 9/1994 | Brougham et al. | |
| 5,357,636 | A * | 10/1994 | Dresdner et al. | 2/161.7 |
| 5,368,867 | A | 11/1994 | Da Silva et al. | |
| 5,419,908 | A | 5/1995 | Richter et al. | |
| 5,437,858 | A | 8/1995 | Hungerbach et al. | |
| 5,508,046 | A | 4/1996 | Cosentino et al. | |
| 5,563,132 | A | 10/1996 | Bodaness | |
| 5,709,870 | A | 1/1998 | Yoshimura et al. | |
| 5,824,267 | A | 10/1998 | Kawasumi et al. | |
| 5,945,032 | A | 8/1999 | Breitenbache et al. | |
| 5,951,993 | A | 9/1999 | Scholz et al. | |
| 5,977,403 | A | 11/1999 | Byers | |
| 5,997,585 | A | 12/1999 | Scialla et al. | |
| 6,027,469 | A | 2/2000 | Johnson | |
| 6,114,298 | A | 9/2000 | Petri et al. | |
| 6,197,814 | B1 | 3/2001 | Arata | |
| 6,200,946 | B1 | 3/2001 | Blum et al. | |
| 6,218,351 | B1 | 4/2001 | Busch et al. | |
| 6,231,848 | B1 * | 5/2001 | Breitenbach et al. | 424/78.24 |
| 6,242,009 | B1 | 6/2001 | Batarseh et al. | |
| 6,257,253 | B1 | 7/2001 | Lentsch et al. | |
| 6,277,414 | B1 | 8/2001 | Elhaik et al. | |
| 6,302,968 | B1 | 10/2001 | Baum et al. | |
| 6,306,812 | B1 | 10/2001 | Perkins et al. | |
| 6,368,611 | B1 | 4/2002 | Whitbourne et al. | |
| 6,379,712 | B1 | 4/2002 | Yan et al. | |

(Continued)

FOREIGN PATENT DOCUMENTS

| | | |
|---|---|---|
| GB | 2189394 | 10/1987 |
| WO | WO 03/080231 | 10/2003 |
| WO | WO 2005/000324 | 1/2005 |
| WO | WO 2006/079109 | 7/2006 |

OTHER PUBLICATIONS

Schuster, A. et al., "Persistent silver disinfectant for the environment: Myth and reality," Am . J. Infect. Control, Jun. 2003, pp. 309-311, vol. 32.

Brady, Michael J. et al., "Persistent silver disinfectant for the environmental control of pathogenic bacteria," Am. J. Infect. Control, Aug. 2004, pp. 208-214, vol. 31 (4).

Brentano, Loreno et al., "Antibacterial efficacy of a colloidal silver complex," Surg. Forum, 1966, pp. 76-78, vol. 17.

Phillips, Charles R., et al., "Chemical Disinfectant," Annual Review of Microbiology, Oct. 1958, pp. 525-550, vol. 12.

Monarca, S. et al, "Decontamination of dental unit waterlines using disinfectants and filters," Abstract Only, Minerva Stomatol., Oct. 2002, vol. 10.

(Continued)

*Primary Examiner*—Charles I Boyer
(74) *Attorney, Agent, or Firm*—Thorpe North & Western LLP

(57) ABSTRACT

The present invention is drawn to disinfectant compositions, which are human safe, e.g., food grade or food safe. In one embodiment, an aqueous disinfectant composition can comprise an aqueous vehicle, including water, from 0.001 wt % to 10.0 wt % of a peroxygen, and an alcohol. Additionally, from 0.001 ppm to 50,000 ppm by weight of a transition metal based on the aqueous vehicle content can also be present. The composition can be substantially free of aldehydes. Alternatively or additionally, the transition metal can be in the form of a colloidal transition metal, such as colloidal silver or alloy thereof.

78 Claims, No Drawings

U.S. PATENT DOCUMENTS

| | | | |
|---|---|---|---|
| 6,436,342 | B1 | 8/2002 | Petri et al. |
| 6,540,791 | B1 | 4/2003 | Dias |
| 6,569,353 | B1 | 5/2003 | Giletto et al. |
| 6,583,176 | B2 | 6/2003 | Arata |
| 6,630,172 | B2 | 10/2003 | Batarseh |
| 6,660,289 | B1 | 12/2003 | Wilmotte et al. |
| 6,743,348 | B2 | 6/2004 | Holladay et al. |
| 6,797,302 | B1 | 9/2004 | Ben Yehuda et al. |
| 6,827,766 | B2 | 12/2004 | Carnes et al. |
| 6,939,564 | B2 | 9/2005 | Ranger et al. |
| 6,939,566 | B2 | 9/2005 | Batarseh et al. |
| 6,962,714 | B2 | 11/2005 | Hei et al. |
| 7,033,511 | B2 | 4/2006 | Zawada et al. |
| 2002/0137648 | A1 | 9/2002 | Sharma et al. |
| 2003/0008797 | A1 | 1/2003 | Hage et al. |
| 2003/0099717 | A1 * | 5/2003 | Cabrera ...................... 424/616 |
| 2003/0235623 | A1 | 12/2003 | Van Oosterom |
| 2004/0067159 | A1 | 4/2004 | Carnes et al. |
| 2004/0170742 | A1 * | 9/2004 | Ben Yehuda et al. ........ 426/615 |
| 2004/0234569 | A1 | 11/2004 | Nakada et al. |
| 2005/0013836 | A1 | 1/2005 | Raad |
| 2005/0194357 | A1 | 9/2005 | Liu et al. |
| 2005/0256017 | A1 | 11/2005 | Dykstra |
| 2005/0256200 | A1 | 11/2005 | Burkhart et al. |
| 2006/0035808 | A1 | 2/2006 | Ahmed et al. |
| 2006/0122082 | A1 | 6/2006 | Paul |
| 2006/0182813 | A1 | 8/2006 | Holladay |
| 2006/0198798 | A1 | 9/2006 | Tichy et al. |
| 2006/0198876 | A1 | 9/2006 | Tichy et al. |
| 2006/0199752 | A1 | 9/2006 | Tichy et al. |
| 2006/0240381 | A1 | 10/2006 | Rizoiu et al. |
| 2006/0263239 | A1 | 11/2006 | Tichy et al. |
| 2007/0048175 | A1 | 3/2007 | Tichy et al. |
| 2007/0059202 | A1 | 3/2007 | Tichy et al. |
| 2007/0059255 | A1 | 3/2007 | Tichy et al. |
| 2007/0254044 | A1 * | 11/2007 | Karandikar et al. ......... 424/618 |
| 2008/0000931 | A1 | 1/2008 | Tichy et al. |

OTHER PUBLICATIONS

Yin, Huiyong, "Analysis of Diacyl Peroxides by Ag+ Coordination Ionspray Tandem Mass Spectrometry: Free Radical Pathways of Complex Decomposition," J. Am. Soc. Mass Spectrum, Apr. 2001, pp. 449-455, vol. 12 (4).

U.S. Appl. No. 11/891,316; Tichy et al. filed Aug. 8, 2007.

Surdeau, N. et al., Sensitivity of bacterial viofilms and planktonic cells to a new antimicrobial agent, Oxsil 320N, Journal of Hospital Infection2006, 62, 487-493, www.elsevierhealth.com/journals/jhin.

http://web.archive.org/web/20060217191603/http://sanosilbiotech.com/start_food.html, Virosil F&B, "Swift Virucidal with Swiss Precision," Feb. 17, 2006, 5 pages.

The interacion of silver ions and hydrogen peroxide in the inactivation of *E coli*: a preliminary evaluation of a new long lasting residual drinking water disinfectant; Water Science and Technology vol. 31 No. 5-6 pp. 123-129 (1995).

* cited by examiner

AQUEOUS SANITIZERS, DISINFECTANTS, AND/OR STERILANTS WITH LOW PEROXYGEN CONTENT

The present application is a continuation-in-part of U.S. patent application Ser. Nos. 11/361,836; 11/361,841; 11/361,837; and 11/361,665, each of which was filed on Feb. 24, 2006, and each of which claims the benefit of U.S. Provisional Patent Application No. 60/656,723, filed on Feb. 25, 2005.

FIELD OF THE INVENTION

The present invention is drawn to consumer safe compositions that can be used for a variety of purposes, including for hard surface cleaning, and which are effective as disinfectants.

BACKGROUND OF THE INVENTION

Disinfectants, such as hard surface disinfectants, are widely used in both domestic and professional settings. Exemplary of a commonly used hard surface cleaner is Lysol® disinfectant. Though Lysol® is effective for many applications, Lysol® is not as effective at reducing levels of bacterial endospores as commercially available glutaraldehyde aqueous solutions. Glutaraldehyde aqueous solutions are widely used as disinfectants, and are commonly available in 1 wt % and 2 wt % solutions, particularly in medical and dental settings. Glutaraldehyde solutions are typically used for more delicate medical/dental instruments that would otherwise be susceptible to damage by other sterilization methods, e.g., autoclaving. However, glutaraldehyde is also a powerful irritant and respiratory sensitizer. In fact, there have been reports of sensitization of individuals due to the fumes, which have lead to respiratory problems, headaches, lethargy, discoloring of the skin, etc. Because of these issues related to glutaraldehyde fumes, air quality must often be monitored, or appropriate air ventilation must be present. As a result, though glutaraldehyde solutions are relatively effective disinfectants, it would be desirable to provide compositions that can exhibit even more effective bacteria kill levels, and at the same time be safer for the individuals using the disinfectant.

SUMMARY OF THE INVENTION

It has been recognized that it would be desirable to provide liquid solution and dispersion disinfectants that are effective for cleaning surfaces, particularly hard surfaces. In accordance with this, an aqueous disinfectant composition can comprise an aqueous vehicle, including water, from 0.001 wt % to 10.0 wt % of a peroxygen, and an alcohol. Additionally, from 0.001 ppm to 50,000 ppm by weight of a transition metal based on the aqueous vehicle content can also be present, with the proviso that the disinfectant composition is substantially free of aldehydes.

In another embodiment, an aqueous disinfectant composition can comprise an aqueous vehicle, including water, from 0.001 wt % to 10.0 wt % of a peroxygen, and an alcohol. The composition can further comprise from 0.001 ppm to 50,000 ppm by weight of a colloidal silver or alloy thereof based on the aqueous vehicle content.

In another embodiment, a method of disinfecting a surface can comprise contacting the surface with a disinfectant composition which comprises an aqueous vehicle, including water, from 0.001 wt % to 10.0 wt % of a peroxygen, and an alcohol. The composition can further comprise from 0.001 ppm to 50,000 ppm by weight of a transition metal or alloy thereof based on the aqueous vehicle content.

Additional features and advantages of the invention will be apparent from the detailed description that follows, which illustrates, by way of example, features of the invention.

DETAILED DESCRIPTION OF THE PREFERRED EMBODIMENT(S)

Reference will now be made to the exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting unless specified as such.

It must be noted that, as used in this specification and the appended claims, the singular forms "a," "an," and "the" include plural referents unless the content clearly dictates otherwise.

The term "food grade" when used with respect to a composition of the present invention refers to a composition that is substantially free from ingredients which would be considered harmful or toxic to a mammal upon consumption above levels that are generally recognized as safe.

Generally, though sanitizers, sterilants, and disinfectants are used for the same purpose, i.e. to kill bacteria and/or viruses, etc., a sterilant composition exhibits a greater kill level compared to a disinfectant, which in turn has a better kill level than a sanitizer. This being stated, most applications require only sanitizer or disinfectant levels bacteria/virus reduction, though other applications benefit considerably from the use of sterilants. For convenience, in the present disclosure, the term "disinfectant" is used generally and includes sanitizers, disinfectants, and sterilants unless the context dictates otherwise.

The term "solution" is also used throughout the specification to describe the liquid compositions of the present invention. However, as these "solutions" can include colloidal transition metals, these compositions can also be described as dispersions or suspensions. As the continuous phase is typically a solution, and the transition metal can be present in ionic and/or colloidal form, for convenience, these compositions will typically be referred to as "solutions" herein.

The term "substantially free" when used with regard to the disinfectant compositions of the present invention refers to the total absence of or near total absence of a specific compound or composition. For example, when a composition is said to be substantially free of aldehydes, there are either no aldehydes in the composition or only trace amounts of aldehydes in the composition.

The term "peroxygen" refers to any compound containing a dioxygen (O—O) bond. Dioxygen bonds, particularly bivalent O—O bonds, are readily cleavable, thereby allowing compounds containing them to act as powerful oxidizers. Non-limiting examples of classes of peroxygen compounds include peracids, peracid salts, and peroxides such as hydrogen peroxide.

When referring to the term "alloy," it is understood that individual colloidal or metallic particles can be in the form of composites of multiple metals, or alloys can also include co-dispersions of multiple metals as separate particles.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc.

In accordance with this, an aqueous disinfectant composition can comprise an aqueous vehicle, including water, from 0.001 wt % to 10.0 wt % of a peroxygen, and an alcohol. Additionally, from 0.001 ppm to 50,000 ppm by weight of a transition metal based on the aqueous vehicle content can also be present, with the proviso that the disinfectant composition is substantially free of aldehydes. In another embodiment, an aqueous disinfectant composition can comprise an aqueous vehicle, including water, from 0.001 wt % to 10.0 wt % of a peroxygen, and an alcohol. The composition can further comprise from 0.001 ppm to 50,000 ppm by weight of a colloidal silver or alloy thereof based on the aqueous vehicle content. In yet another embodiment, a method of disinfecting a surface can comprise contacting the surface with a disinfectant composition which comprises an aqueous vehicle, including water, from 0.001 wt % to 10.0 wt % of a peroxygen, and an alcohol. The composition can further comprise from 0.001 ppm to 50,000 ppm by weight of a transition metal or alloy thereof based on the aqueous vehicle content.

It is noted that the lower end of the range of the peroxygen can be modified to 0.05 wt % or 0.1 wt %, and/or the upper end of the range can be modified to 5 wt %, 3 wt %, or 1.5 wt % in accordance with specific embodiments of the present invention. It is also noted that the alcohol is given herein without a range limitation, but in one embodiment, can be present at from 0.001 wt % to 95 wt %. This being stated, the lower end of the range of the alcohol can be modified to 0.05 wt % or 0.1 wt %, and the upper end of the range can be modified to 40 wt %, 30 wt %, 20 wt % or 10 wt % in accordance with specific embodiments of the present invention. Further, the concentration of the metal content, including ionic and/or colloidal content, can also be modified to 10 ppm by weight at the lower end of the range, and/or to 10,000 ppm, 5,000 ppm, or 1500 ppm by weight at the upper end of the range. As these ranges are merely exemplary, one skilled in the art could modify these ranges for a particular application, considering such things as the type of alcohol (polyhydric, food grade, mixtures, etc.); the type of peroxygen (peroxide, peracid, combination of peroxide/peracid, etc.); and the type of metal (ionic, colloidal, alloy, etc.).

In one embodiment, the disinfectant composition can include only ingredients that are food-grade or food safe. For example, though not required, the composition can be substantially free of disinfectant ingredients commonly present in many commercially available surface cleaners. Examples of non-food-grade ingredients which can be omitted from the disinfectants of the present invention include, but are not limited to, aldehydes such as glutaraldehyde; chlorine-based disinfectants; chlorine and bromine-based disinfectants; iodophore-based disinfectants; phenolic-based disinfectants, quaternary ammonium-based disinfectants; and the like.

The aqueous vehicle can optionally include other ingredients, such as organic co-solvents. In particular, certain alcohols can be present. For example, alcohols, including aliphatic alcohols and other carbon-containing alcohols, having from 1 to 24 carbons ($C_1$-$C_{24}$ alcohol) can be used. It is to be noted that "$C_1$-$C_{24}$ alcohol" does not necessarily imply only straight chain saturated aliphatic alcohols, as other carbon-containing alcohols can also be used within this definition, including branched aliphatic alcohols, alicyclic alcohols, aromatic alcohols, unsaturated alcohols, as well as substituted aliphatic, alicyclic, aromatic, and unsaturated alcohols, etc. In one embodiment, the aliphatic alcohols can be $C_1$ to $C_5$ alcohols including methanol, ethanol, propanol and isopropanol, butanols, and pentanols, due to their availability and lower boiling points. This being stated, polyhydric alcohols can also be used effectively in enhancing the disinfectant and sterilant potency of the compositions of the present invention, as well as provide some degree of added stabilization. Examples of polyhydric alcohols which can be used in the present invention include but are not limited to ethylene glycol (ethane-1, 2-diol) glycerin (or glycerol, propane-1,2,3-triol), and propane-1,2-diol. Other non-aliphatic alcohols may also be used including but not limited to phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z,12Z-octadecadien-1-ol), elaidyl alcohol (9E-octadecen-1-ol), elaidolinoleyl alcohol (9E,12E-octadecadien-1-ol), linolenyl alcohol (9Z,12Z,15Z-octadecatrien-1-ol), elaidolinolenyl alcohol (9E,12E,15-E-octadecatrien-1-ol), combinations thereof, and the like.

In some embodiments, for practical considerations, methanol, ethanol, and denatured alcohols (mixtures of ethanol and smaller amounts of methanol, and optionally, minute amounts of benzene, ketones, acetates, etc.) can often be preferred for use because of their availability and cost. Glycerol is also useable in some embodiments. If the desire is to provide a food grade composition, then alcohols can be selected that satisfy this requirement. When considering the amount of alcohol to use, one skilled in the art can stay within the above-described ranges, or modify these ranges for a particular application, considering such things as whether alcohol selected for use is polyhydric, whether the alcohol is food grade, mixtures of alcohols, etc.

Regarding the transition metal, in accordance with the embodiments of the present invention, the metal can be in ionic form (e.g. disassociate metal salt, metal ions from elemental metal, etc.) and/or in colloidal form. In one specific embodiment, the transition metal can be in a sub-micron form (i.e. dispersion of less than 1 μm metal colloidal particles). However, larger colloidal transition metal particles can also be used in certain applications. Typical transition metals that are desirable for use include Group VI to Group XI transition metals, and more preferably, can include Group X to Group XI transition metals. Alloys including at least one metal from the Group VI to Group XI metals can also be used. It is recognized that any of these metals will typically be oxidized to the corresponding cation in the presence of a peroxygen. However, with colloidal metals, typically, the surface is usually more susceptible to such oxidation. Further, when colloidal metals are dispersed in a colloidal solution, there is often an amount of the metal in ionic or salt form that is also present in the suspension solution. For example, colloidal silver may include a certain percentage of silver salt or ionic silver in solution, e.g., 10% to 90% by weight of metal content can be ionic based on the total metal content. This being stated, certain preferred metals for use in accordance with embodiments of the present invention are ruthenium, rhodium, osmium, iridium, palladium, platinum, copper, gold, silver, alloys thereof, and mixtures thereof. Silver is often the most preferred, but metal choice can be dependent to some degree on the application, the levels of kill desired or required, the type of pathogen being targeted, the substrate that is being cleaned, etc.

It is also noted that any of these embodiments can often also benefit from the use of alloys. For Example, certain combinations of metals in an alloy may provide an acceptable kill level for a specific pathogen, and also provide benefits that are related more to secondary consideration, such as solution stability, substrate to be cleaned, etc. Preferred examples of transition metal alloys for use in the present invention include but are not limited to copper-silver alloys, silver-manganese alloys, iron-copper alloys, chromium-silver alloys, gold-silver alloys, magnesium-silver alloys, and the like.

Exemplary colloidal silvers that can be used include those sold by Solutions IE, Inc. under the trade names CS Plus and C S Ultra. Other colloidal silver products that can be used as the silver source include ASAP, Sovereign Silver, Silver Max, and the like. In one embodiment, the colloidal particles used in the present invention can have a particle size range of from 0.001 μm to 1.0 μm. In another embodiment the colloidal transition metal particles can have a size range of from 0.030 μm to 0.5 μm. In still another embodiment the average particle size is 0.35 μm to 0.45 μm. If used in ionic form, preferred silver salts include but are not limited to silver nitrate, silver acetate, silver citrate, silver oxide, and/or silver carbonate. Though many colloidal silver solutions or ionic silver solutions that are functional for use in the formulations of the present invention can be used, in one embodiment, it can be desirable to use RO water as the suspension medium for the colloidal and/or ionic silver that is mixed with the other ingredients. In a more detailed aspect, the RO water can also be distilled, resulting in 18-20 MΩ water, though this is not required.

The peroxygen component of the disinfectant solution can be a single compound or a combination of multiple peroxygen compounds or peroxygen forming compounds. In one embodiment, the peroxygen can be any aliphatic or aromatic peracid (or peroxyacid) that is functional for disinfectant purposes in accordance with embodiments of the present invention. While any functional peroxyacid can be used, peroxyacids containing from 1 to 7 carbons are the most practical for use. These peroxyacids can include, but not be limited to, peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, and/or peroxybenzoic acid. The peroxyacid used in the present invention can be prepared using any method known in the art. When the peroxyacid is prepared from an acid and hydrogen peroxide, the resultant mixture contains both the peroxyacid and the corresponding acid that it is prepared from. For example, in embodiments that utilize peroxyacetic acid, the presence of the related acid (acetic acid) provides stability to the mixture, as the reaction is an equilibrium between the acid, hydrogen peroxide, and the peroxyacid and water, as follows:

$$H_2O_2 + CH_3COOH \longleftrightarrow CH_3COO{-}OH + H_2O$$

Peracid salts, such as salts of the above listed peracids, can also be included as the peroxygen component of the disinfectant solutions. Non-limiting examples of such salts include permanganates, perborates, perchlorates, peracetates, percarbonates, persulphates, and the like. The salts can be used alone or in combination with each other or other peroxygen compounds to form the peroxygen component of the invention.

In another embodiment, the peroxygen component of the invention can include a peroxide compound. While hydrogen peroxide is considered to be a desirable peroxide for use in accordance with embodiments of the present invention, other peroxides can also be used, such as metal peroxides and peroxyhydrates. The metal peroxides that can be used include, but are not limited to, sodium peroxide, magnesium peroxide, calcium peroxide, barium peroxide, and/or strontium peroxide. Other salts (for example sodium percarbonate) have hydrogen peroxide associated therewith much like waters of hydration, and these could also be considered to be a source of hydrogen peroxide, thereby producing hydrogen peroxide in situ. As mentioned above, the peroxides can be used alone or in combination with other peroxygen compounds to form the peroxygen component of the present invention.

The disinfectant compositions of the present invention can be incorporated with other ingredients to form a variety of disinfectant products including but not limited to hand cleansers, mouthwashes, surgical scrubs, body splashes, hand sanitizer gels and foams, disinfectant wipes, and similar personal care products. Additional types of products include disinfectant foams, creams, mousses, and the like, and compositions containing organic and inorganic filler materials, such as emulsions, lotions, creams, pastes, and the like. The compositions further can be used as an antibacterial cleanser for hard surfaces, for example, in bathrooms, hospitals, sinks and countertops, food service areas, and meat processing plants. The disinfectant compositions can also be used as disinfectant fogs and disinfectant mists. The present antibacterial compositions can be manufactured as dilute ready-to-use compositions, or as concentrates that can be diluted prior to use. The various products in which the disinfectants are used may also include fragrances, depending on the nature of the product. For example, a pine or lemon fragrance may be desirable for use for kitchen cleaning wipes because of their appealing association with cleanliness to many consumers. Further, gels or aerosols may also be fragranced for similar or other reasons.

In one embodiment of the present invention, the disinfectant compositions are used to make disinfectant wipes. The disinfectant wipes of the present invention can be used to clean a variety of hard and other surfaces, including human hands and skin, medical instruments, countertops, sinks, floors, walls, windows, etc. The wipes of the present invention can be made of a variety of fabrics. For the purposes of the present invention, fabrics can include cloths and papers, as well as woven and non-woven materials. The woven or non-woven fabrics can be made of suitable materials such as rayon, nylon, or cotton, combinations thereof. Examples of nonwoven fabrics are described in U.S. Pat. Nos. 3,786,615; 4,395,454; and 4,199,322; which are hereby incorporated by reference. The fabrics or papers can be impregnated with the disinfectant solution by any method known in the art. The wipes can be packaged in any manner known in the art including individual blister-packs or wrapped or stacked multi-packs.

In another embodiment, the disinfectant composition of the present invention is formulated into a gel or gelatinous sanitization composition. In addition to the disinfectant compositions, the gel sanitizers of the present invention can include a thickening or gelling agent, wherein "thickening agent" and "gelling agent" are used interchangeably. For the purposes of the present invention, the terms "gel" or "gelatinous" sanitization compositions refers to a disinfectant liquid substances that can have a viscosity from about 1,000 centipoise to about 100,000 centipoise, or from 2,000 centipoise to 50,000 centipoise in another embodiment, though these ranges are not intended to be limiting. For example, a hand gel may be considerably less viscous than a gel used for industrial cleaning or disinfectant purposes. Examples of gelling or thickening agents include but are not limited to natural gum such as guar and guar derivatives, a synthetic polymer, a clay, an oil, a wax, aloe vera gel, an acrylate homopolymer, an acrylate copolymer, a carbomer, cellulose, a cellulose derivative, algin, an algin derivative, a water-insoluble $C_8$-$C_{20}$ alcohol, carrageenan, fumed silica, mixtures thereof, and the like. The gelling agent can be present in the gelatinous sanitation composition in an amount from about 0.1 wt % to 50 wt % of the gelatinous composition. In another embodiment, the gelling agent is present in an amount from 0.25 wt % to 10 wt % of the gelatinous composition. The amount of gelling agent can be dependent on a variety of factors including the type of gelling agent and the desired viscosity of the gel. The gelatinous sanitizers can be used for a variety of applications including sanitization of human skin e.g., gel hand sanitizer, and hard surface sanitation. In one particular embodiment, the disinfectant composition can be mixed with natural aloe gel to form a disinfectant aloe formulation. Such a formulation would be useful for application to burns, skin infections, and other irritations. The aloe may act as a thickening agent, or may also include another thickening or gelling agent as described above, depending on the desired viscosity of the disinfectant gel.

In another embodiment, the disinfectant composition of the present invention can be formulated into a disinfectant foam or foaming composition. The disinfectant foams or foaming compositions include the disinfectant composition and foaming agents. Any foaming agent known in the art can be used depending on the desired application and characteristics of the resulting disinfectant foam. As with the disinfectant composition, the disinfectant foams of the present invention can be used in both human (e.g. hand washing) and industrial applications.

In another embodiment, the disinfectant composition of the present invention can be in the form of a disinfectant aerosol or fog. Fogging, also referred to as thermal fogging, is the process by which disinfectants are aerosolized. The aerosol particles of the disinfectant are suspended within the air for a period of time in order to disinfect both the air itself and surfaces, including inaccessible parts of a structure such as air vents. The aerosolized particles of disinfectant can have a particle size of from about 5 μm to about 200 μm. In another embodiment, the aerosolized particle can have a particle size of from about 20 μm to about 150 μm. When the aerosolized disinfectant contains a colloidal transition metal, the aerosolized particles are typically of sufficient size to contain at least 1 of the colloidal transition metals, though typically, each aerosolized particle will contain multiple colloidal transition metal particles.

Fogging is often a last stage of a complete biosecurity program, and as such, can have a major part to play in disease prevention and control. Traditional fogging agents such as formaldehyde, glutaraldehyde, or glutaraldehyde can pose major health and safety issues to persons who come in contact with the disinfectant. As the disinfectants of the present invention can be formulated to use only food-grade ingredients, their use in disinfectant fogging is of great value. Most fogging machines work by using high volumes of air under great pressure to generate small droplets. The disinfectants compositions of the present invention are compatible with most standard fogging machines. Examples of suitable fogging machines include Dyna-Fog's® Thermal Foggers and Cold Foggers.

As a solution, the composition can be used as a liquid dispersion bath for objects such as instruments or as a spray for applying to less mobile objects. The disinfectant solution can also be used as a topical dressing or a mouthwash. In other words, any application method known by those skilled in the art can be utilized in accordance with embodiments of the present invention.

The disinfectant compositions of the present invention can be prepared for application by any of a number of methods. For example, the composition can be prepared as a solution, gel, foam, fog, etc. As a solution, the composition can be used as a liquid dispersion bath for dipping instruments or other objects, as a spray for applying to less mobile objects, as a wipe where the liquid dispersion is applied to a fabric or fabric-like material for easy application without the need for spray or other application methods, as a topical dressing, as a mouthwash, etc. In other words, any application method known by those skilled in the art can be utilized in accordance with embodiments of the present invention.

Additionally, though the compositions of the present invention are described generally as disinfectants, sterilants, or sanitizers, it is recognized that there are many possible applications. For example, without limitation, the compositions of the present invention can be used to kill bacteria, spores, viruses, parasites, funguses, and molds. As described, this composition can be used against all of these types of organisms with relative to complete safety to humans and other mammals.

Because these compositions can be formulated to be very safe, e.g., often including only food grade components, these compositions can be used in areas which extend well beyond their use as hard surface disinfectants. Such product categories include both topically and internally applied products for both humans and animals. For example, these compositions can be used for antiseptics, burn treatments, diaper rash products, and various skin care products. Alternatively, these compositions can be used inside the mouth, such as for mouthwashes, toothpastes, and various other disinfecting solutions that are be employed in dental mold materials. As dental molds are known to spread significant disease in the dental industry, such use with dental molds can prevent or reduce the spread of pathogens from a patient's mouth to lab employees working with the finished molds. Still a further category of use includes application for antibiotic and antiviral purposes. These compositions can be formulated into lozenges or gums for application to the mouth and throat, and can even be administered orally, intramuscularly, intravenously, etc. Because of the kill levels that can be achieved, even when formulated with only food grade components, a wide range of pathogens, as well as some viruses, can be killed internally. Without being bound by any particular possibility, these compositions can be useful in killing various viruses such as HIV, SARS, West Nile, Bird Flu, and others.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Preparation of Disinfectant

An aqueous disinfectant composition is prepared in accordance with embodiments of the present invention, which includes the following ingredients in approximate amounts: 9 wt % ethanol; 1.3 wt % peroxyacetic acid (from a 6 wt % solution); less than 3 wt % hydrogen peroxide to stabilize the peroxyacetic acid; and the balance being water containing 600 ppm colloidal silver. It is noted that there will be less than 600 ppm by weight of the colloidal silver when based on the aqueous vehicle content as a whole.

Example 2

Preparation of Disinfectant

An aqueous disinfectant composition is prepared in accordance with embodiments of the present invention, which includes the following ingredients in approximate amounts: 9 wt % isopropanol; 1.3 wt % peroxypropanoic acid (from a 6 wt % solution); less than 3 wt % of a peroxide, e.g., sodium peroxide, to stabilize the peroxypropanoic acid; and the balance being water containing 600 ppm ionic silver. It is noted that there will be less than 600 ppm by weight of the ionic silver when based on the aqueous vehicle content as a whole.

Example 3

Preparation of Disinfectant

An aqueous disinfectant composition is prepared in accordance with embodiments of the present invention, which includes the following ingredients in approximate amounts: 20 wt % denatured alcohol; 5 wt % peroxyformic acid; and the balance being water containing 10,000 ppm by weight colloidal silver and copper alloy. Small amounts of hydrogen peroxide and formic acid are also added to the composition as a whole to stabilize the peroxyformic acid. It is noted that there will be less than 10,000 ppm by weight of the colloidal silver when based on the aqueous vehicle content as a whole.

Example 4

Preparation of Disinfectant

An aqueous disinfectant composition is prepared in accordance with embodiments of the present invention, which includes the following ingredients in approximate amounts: 9 wt % ethanol; 1.3 wt % peroxyacetic acid (from a 6 wt % solution); less than 3 wt % hydrogen peroxide to stabilize the peroxyacetic acid; and the balance being water containing 80 ppm colloidal silver. It is noted that there will be less than 80 ppm by weight of the colloidal silver when based on the aqueous vehicle content as a whole.

Example 5

Preparation of Disinfectant

An aqueous disinfectant composition is prepared in accordance with embodiments of the present invention, which includes the following ingredients in approximate amounts: 10 wt % glycerol; 1.3 wt % peracetic acid; and the balanced being water with approximately 300 ppm colloidal silver. It is noted that there will be less than 300 ppm by weight of the colloidal silver when based on the aqueous vehicle content as a whole.

Example 6

Preparation of Disinfectant

An aqueous disinfectant composition is prepared in accordance with embodiments of the present invention, which includes the following ingredients in approximate amounts: 10.0 wt % glycerol; 1.8 wt % percitric acid; and the balance being water with approximately 300 ppm colloidal silver. It is noted that there will be less than 300 ppm by weight of the colloidal silver when based on the aqueous vehicle content as a whole.

Example 7

Preparation of Disinfectant

An aqueous disinfectant composition is prepared in accordance with embodiments of the present invention, which includes the following ingredients in approximate amounts: 8.5 wt % 1 -propanol; 1.3 wt % peracetic acid; and the balance being RO water (reverse osmosis water) containing about 300 ppm by weight colloidal silver. It is noted that there will be less than 300 ppm by weight of the colloidal silver when based on the aqueous vehicle content as a whole.

Example 8

Preparation of Disinfectant

An aqueous disinfectant composition is prepared in accordance with embodiments of the present invention, which includes the following ingredients in approximate amounts: 40 wt % glycerol; 8 wt % percitric acid; and the balance being RO water (reverse osmosis water) containing about 300 ppm by weight colloidal silver. It is noted that there will be less than 300 ppm by weight of the colloidal silver when based on the aqueous vehicle content as a whole.

Example 9

Preparation of Disinfectant

An aqueous disinfectant composition is prepared in accordance with embodiments of the present invention, which includes the following ingredients in approximate amounts: 8.5 wt % glycerol; 0.4 wt % peracetic acid; and the balance being RO water (reverse osmosis water) containing 300 ppm by weight colloidal silver. It is noted that there will be less than 300 ppm by weight of the colloidal silver when based on the aqueous vehicle content as a whole.

Example 10

Kill-Time Studies of *Staphylococcus aureus* Using Disinfectant of Example 1

A study was conducted to determine the antimicrobial activity of the colloidal silver-containing disinfectant of Example 1, when challenged with an organic load, on the test organism *Staphylococcus aureus*. This was accomplished by performing a standard suspension test on the disinfectant containing 5% v/v horse serum. A 15 second contact time was evaluated.

Specifically, the test suspension was prepared by growing a 5 ml culture of *Staphylococcus aureus*, ATCC 6538, in Todd Hewitt Broth at 37° C., for 20 hours. Five (5) ml of culture was pelleted by centrifugation, washed with 5 ml sterile 18 MΩ water, centrifuged again, and resuspended in a final volume of 5 ml sterile water.

A neutralizer was prepared that consisted of 9 ml tubes of 12.7 wt % Tween 80 (surfactant), 6.0 wt % Tamol, 1.7 wt % lecithin, 1 wt % peptone, and 0.1 wt % cystine, to which was added 10 pd of catalase solution (Sigma, C100, 42,300 units/mg).

The "Kill Time" procedure followed was as follows: A 9.9 ml aliquot of the disinfectant of Example 1 (containing 5% v/v horse serum) was placed in a sterile 20 mm×150 mm tube, and the tube was equilibrated in a 20° C. water bath. The tube of disinfectant was inoculated with 100 μl of the test organism suspension at time zero. After 15 seconds, 1 ml of the organism/disinfectant suspension was removed to 9 ml of neutralizer. After 2 minutes, the neutralized suspension was serially diluted ($1{:}1\times10$, $1{:}1\times10^2$, $1{:}1\times10^3$, etc.) in physiological saline solution (PSS). The number of viable organisms in selected dilution tubes was assayed by membrane filtration. One (1) ml aliquots were plated in duplicate, and the membranes were washed with about 100 ml of sterile PSS and removed to Columbia agar plates. The plates were incubated at 37° C. for 20 hours. The number of colonies on each filter was counted and log reduction and percent kill values were computed.

As a control, a titer (or measurement of the amount or concentration of a substance in a solution) of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 μl of the $1{:}10^5$ dilution of the titer. This produced about 1,500 CFU/ml in the tube, which was allowed to stand for 20 minutes prior to dilution and assay of the tubes by membrane filtration using duplicate 1 ml samples. Sterilization controls were performed by filtering 100 ml (PSS) or 1 ml (other fluids) samples of each solution used in this testing. Plates were incubated as above.

The results are provided as follows:

TABLE 1a

Titer

| | Dilution | | |
|---|---|---|---|
| | $1{:}1\times10^5$ | $1{:}1\times10^6$ | $1{:}1\times10^7$ |
| Number of Colonies | TNC* | TNC | 111 |
| | TNC | TNC | 89 |

*TNC—Too Numerous to Count

TABLE 1b

Disinfectant solution (Example 1 solution with 5% v/v horse serum)
Dilution of *staphylococcus*/disinfectant suspension

| | Dilution | | |
|---|---|---|---|
| | $1{:}1\times10^1$ | $1{:}1\times10^2$ | $1{:}1\times10^3$ |
| 15 Seconds | 0 | 0 | 0 |
| | 0 | 0 | 0 |

TABLE 1c

Neutralization control

| | Dilution | |
|---|---|---|
| | undilute | $1{:}1\times10^1$ |
| 15 Seconds | TNC | 156 |
| | TNC | 148 |

Sterilization controls indicated zero growth for the neutralizer, water, PSS, Columbia agar, disinfectant, and horse serum. Results of the titer showed a viable staphylococcus concentration of $1\times10^{10}$ organisms per ml in the original suspension. Inoculation of 9.9 ml of disinfectant with 100 μl of this suspension produced an initial concentration of $1\times10^8$ organisms per ml in the assay tube. Results from these procedures allowed log reduction (LR) and percent kill (PK) values to be calculated using the formulas: 1) $LR=-Log(S/So)$ where S=concentration of viable organisms after 45 minutes; and So=the initial concentration of viable organisms at time zero; and 2) $PK=(1-(S/So))\times100$. These values are shown below.

TABLE 2

Results

| Solution | Contact Time | Log Reduction (LR) | Percent Kill (PK) |
|---|---|---|---|
| Disinfectant solution of Example 1 with 5% v/v horse serum | 15 sec | >7.00 | >99.99999 |

The neutralization control data indicated that the test solution was adequately neutralized. Observed counts were slightly greater than those expected, indicating no residual killing took place due to un-neutralized disinfectant. In general, the disinfectant solution tested here had high antimicrobial activity against Staphylococcus aureus. It is significant to note that this level of activity was achieved even though the disinfectant was premixed with an organic load consisting of 5% v/v horse serum. An organic load (such as 5% v/v horse serum) will often adversely affect the antimicrobial action of disinfectants. The solution of Example 1 was nevertheless able to effect greater than a 7 log reduction of viable organisms within 15 seconds, even in the presence of 5% v/v horse serum.

Example 11

Kill-Time studies of *Bacillus subtilis* using Disinfectant of Example 6

A study was conducted to determine the antimicrobial activity of the colloidal silver-containing disinfectant of Example 6, on bacterial endospores from the test organism *Bacillus subtilis*. This was accomplished by performing a standard kill-time suspension test using a suspension of *B. subtilis* endospores.

Specifically, the test suspension containing endospores from *B. subtilis* was prepared from a culture grown for three days at 37° C. in Leighton-Doi medium. The suspension was placed at 65° C. for 30 minutes to kill vegetative organisms, and then centrifuged to pellet the spores. Spores were resuspended in sterile HPLC water and allowed to set overnight at 4° C. This washing/setting process was repeated a total of three times. The final spore suspension was examined for purity using phase-contrast microscopy and stored at 4° C. until it was used.

A neutralizer was prepared that consisted of 9 ml tubes of 12.7 wt % Tween 80 (surfactant), 6.0 wt % Tamol, 1.7 wt % lecithin, 1 wt % peptone, and 1.0 wt % cystine and 500 mM Tris (pH 7.85), to which 100 μl of catalase solution (Sigma C100, 42,300/mg) was added immediately before use.

The "Kill Time" procedure followed was as follows: A 9.9 ml aliquot of the disinfectant of Example 6 (containing 5% v/v horse serum) was placed in a sterile 50 ml polypropylene centrifuge tube, and the tube was equilibrated in a 20° C. water bath. The tube of disinfectant was inoculated with 100 μl of the spore/disinfectant suspension at time zero. After 60 seconds, 1 ml of the spore/disinfectant suspension was removed to 9.1 ml of neutralizer. After 2 minutes, the neutralized suspension was serially diluted (1:×10, 1:1×$10^2$, 1:1×$10^3$, etc.) in physiological saline solution (PSS). The number of viable spores in selected dilution tubes was assayed by membrane filtration. One (1) ml aliquots were plated in duplicate, and the membranes were washed with about 100 ml of sterile PSS and removed to Columbia agar plates. The plates were incubated at 37° C. for 20 hours. The number of colonies on each filter was counted and log reduction and percent kill values were computed.

As a control, a titer (or measurement of the amount or concentration of a substance in a solution) of the test suspension was computed by performing membrane filtration assays of selected 1:10 dilutions of the test suspension in PSS. A neutralizer control was performed by inoculating a mixture of 9.1 ml of neutralizer and 1 ml of disinfectant with 100 μl of the 1:$10^6$ dilution of the titer. This produced about 96 CFU/ml in the tube, which was allowed to stand for 20 minutes prior to dilution and assay of the tubes by membrane filtration using duplicate 1 ml samples. Sterilization controls were performed by filtering 100 ml (PSS) or 1 ml (other fluids) samples of each solution used in this testing. Plates were incubated as above.

The results are provided as follows:

TABLE 15a

| Titer | | | |
|---|---|---|---|
| | Dilution | | |
| | 1:1 × $10^7$ | 1:1 × $10^8$ | 1:1 × $10^9$ |
| Number of Colonies | TNC* | 78 | 12 |
| | TNC | 74 | 5 |

*TNC—Too Numerous to Count

TABLE 15b

| Disinfectant solution (Example 6 solution) Dilution of *B. subtilis* spores/disinfectant suspension | | | | |
|---|---|---|---|---|
| | Dilution | | | |
| | 1:1 × $10^2$ | 1:1 × $10^3$ | 1:1 × $10^4$ | 1:1 × $10^5$ |
| 3 minutes | TNC | TNC | 209 | 30 |
| | TNC | TNC | 331 | 34 |

TABLE 15c

| Disinfectant solution (Example 6) Dilution of *B. subtilis* spores/disinfectant suspension | | | | |
|---|---|---|---|---|
| | Dilution | | | |
| | 1:1 × $10^2$ | 1:1 × $10^3$ | 1:1 × $10^4$ | 1:1 × $10^5$ |
| 10 minutes | 0 | 0 | 0 | 0 |
| | 0 | 0 | 0 | 0 |

TABLE 15d

| Neutralization control Undiluted |
|---|
| 76 |
| 83 |

TABLE 15e

| Sterility controls | |
|---|---|
| Material | Counts |
| Example 6 Disinfectant | 0 |
| Neutralizer | 0 |
| Columbia Agar | 0 |
| Physiological sterile saline | 0 |

Results of the titer showed a viable *B. subtilis* spore concentration of 9.80×$10^9$ spores per ml in the original suspension. Inoculation of 9.9 ml of disinfectant with 100 μl of this suspension produced an initial concentration of 9.80×$10^7$ spores per ml in the assay tube. Results from these procedures allowed log reduction (LR) and percent kill (PK) values to be calculated using the formulas: 1) LR=−Log(S/So) where S=concentration of viable organisms after 45 minutes; and So=the initial concentration of viable organisms at time zero; and 2) PK=(1−(S/So))×100. These values are shown below.

TABLE 16

| Results | | | |
|---|---|---|---|
| Solution | Contact Time | Log Reduction (LR) | Percent Kill (PK) |
| Disinfectant solution of Example 6 | 3 minutes | 1.38 | 95.79 |
| Disinfectant solution of Example 6 | 10 minutes | >7.18 | 99.999993 |

The neutralization control data indicated that the test solution was adequately neutralized. Observed counts were similar to, or higher than those expected, indicating no residual killing took place due to un-neutralized disinfectant. The disinfectant solution of Example 6 had good sporicidal activity, effecting a 1.38 log reduction within 3 minutes and greater than 7 log reduction in 10 minutes. It is worth noting that *B. subtilis* is a common species used in sporacidal testing and belongs to the same genus as the organism that causes anthrax. Because of their similarities, *B. subtilis* spores have been used as non-pathogenic surrogates for spores of *Bacillus anthracis*.

Example 12

Kill-Time Studies of *Mycobacterium bovis* Using the Disinfectant Solution of Example 5

A study was conducted to determine tuberculocidal activity of the disinfectant solution of Example 5 on a hard surface using the CRA Environmental Wipe Method. This method is fully described in: Christensen, R. P., R. A. Robison, D. F. Robinson, B. J. Ploeger, R. W. Leavitt, and H. L. bodily, Antimicrobial Activity of Environmental Surface Disinfecants in the Absence and Presence of Bioburden. Journal of the American Dental Association, 119:493-505. 1989.

Specifically, a test suspension containing *Mycobacterium bovis* (ATCC # 35743) was prepared from a frozen suspension of a standardized culture grown in modified Proskauer-Beck medium. The suspension was thawed and mixed with an equal volume of phosphate-buffered gelatin solution in a Teflon-on-glass tissue grinder on ice. The suspension was homogenized for two minutes, then diluted 1:4 in physiological saline solution (PSS) containing 0.1% Tween 80. The suspension was vortexed and held on ice until used in inoculate the test surface.

A neutralizer mixture consisted of 50 ml flasks of Tryptic soy broth containing 1.0% Tween 80, 1.0% lecithin, and 50 μl of concentrated catalase solution (Sigma, C100, 42,300 units/mg).

The CRA environmental Wipe Method which was used is detailed below. An 8×12 inch piece of laminated plastic counter covering was secured to polypropylene dental trays (size B, Zirc Dental) with silicone adhesive. Lids and trays were sterilized by a hydrogen peroxide gas plasma sterilizer. Two ml of test organism suspension was applied to the surface with a sterile2×2-in cotton-filled gauze sponge. The surface was allowed to dry 20-30 minutes in a biosafety cabinet under laminar flow. Then 3.5 ml of disinfectant (or water) was applied to a sterile gauze sponge, which was used to wipe the inoculated test surface for 10 seconds using about 150-g pressure with overlapping strokes (20 left to right, followed by 20 top to bottom). After 3 minutes, the trays were flooded with 50 ml of neutralizer and scrubbed for 1 minute with a sterile polypropylene brush to remove and suspend organisms. The fluid was collected and serially diluted 1:10 in physiological saline solution (PSS). The number of viable organisms in selected dilution tubes was assayed by membrane filtration. One ml aliquots were plated in duplicate. The membranes were washed with about 100 ml of sterile PSS and removed to Mycobacteria 7H11 agar plates. The plates were incubated at 37° C. for about three weeks. The number of colonies on each was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 μl of the 1:$10^3$ dilution of the titer containing 1750 CFU. This produced 175 CFU/ml in the tube, which was allowed to stand for 20 minutes prior to dilution and assay of the tubes by membrane filtration using duplicate 1 ml samples.

The results are provided as follows:

TABLE 19a

| *Mycobacterium bovis* Titer | | | |
|---|---|---|---|
| | Dilution | | |
| | 1:1 × $10^3$ | 1:1 × $10^4$ | 1:1 × $10^5$ |
| Number of | TNC* | TNC | 175 |
| Colonies | TNC | TNC | 174 |

*TNC—Too Numerous to Count

TABLE 19b

| Disinfectant solution of Example 5<br>Dilution of *M. bovis*/disinfectant suspension | | | | |
|---|---|---|---|---|
| | Dilution | | | |
| | Undiluted | 1:1 × $10^1$ | 1:1 × $10^2$ | 1:1 × $10^3$ |
| 3 minutes | 1 | 0 | 0 | 0 |
| | | 0 | 0 | 0 |

TABLE 19c

| Neutralization control<br>Undiluted |
|---|
| 75 |
| 66 |

TABLE 19d

| Sterility controls | |
|---|---|
| Material | Counts |
| Phosphate buffered gelatin | 0 |
| Neutralizer + catalas | 0 |
| Example 5 Disinfectant | 0 |
| Mycobacteria 7H11 Agar | 0 |
| Physiological sterile saline (PSS) + 0.1% Tween 80 | 0 |
| Physiological sterile saline (PSS) | 0 |

Results of the titer showed the initial concentration of *M. bovis* was 1.75×107 CFU per ml in the prepared suspension. Inoculation of the test surface following drying produced a challenge exhibited by the water control. The initial concentration of viable bacilli on the test surface (So) was 2.63×$10^5$. Results from these procedures allowed log reduction (LR) and percent kill (PK) values to be calculated using the formulas: 1) LR=−Log(S/So) where S=concentration of viable organisms after a period of exposure to the disinfectant; and So=the initial concentration of viable organisms at time zero; These values are shown in the Table 20 below.

TABLE 20

| Results | | | |
|---|---|---|---|
| Solution | Contact Time | Log Reduction (LR) | Percent Kill (PK) |
| Example 5 | 3 minutes | 5.02 | 99.99905 |

The neutralization control data indicated that each test solution was adequately neutralized. Observed counts were similar to those expected from the titer data.

Example 13

Kill-Time Studies of Sporicidal Activity Using Various Disinfectant Solutions

A study was conducted to determine the antimicrobial activity of the silver-containing disinfectant of Example 5 on bacterial endospores from the test organism *Bacillus subtilis*. This was accomplished by performing a standard kill-time suspension test using a suspension of *B. subtilis* endospores. In general, spores are much more difficult to kill than common bacteria.

The test suspension containing endospores from *Bacillus subtilis* (ATCC # 19659) was prepared from a culture grown for three days at 37° C. in Leighton-Doi medium. The suspension was placed at 65° C. for 30 minutes to kill vegetative organisms, then centrifuged to pellet the spores. Spores were resuspended in sterile HPLC water and allowed to set overnight at 4° C. This washing/setting process was repeated a total of three times. The final spore suspension was examined for purity using phase-contrast microscopy and stored at 4° C. until used.

A neutralizer solution was also prepared that consisted of 9 ml tubes of 12.7 wt % Tween 80, 6.0 wt % Tamol, 1.7 wt % lecithin, 1 wt % peptone, and 1.0 wt % cystine, and 500 mM tris (pH 7.85), to which 100 µl of catalase solution (Sigma, C100, 42,300 units/mg) was added immediately before use.

The "kill time" procedure was as follows: A 9.9 ml aliquot of the disinfectant was placed in a 50 ml polypropylene sterile centrifuge tube. The tube was equilibrated in a 20° C. water bath. The tube of disinfectant was inoculated with 100 µl of the spore suspension at time zero. After a 30 second contact time, one ml of spore/disinfectant suspension was removed to 9.1 ml of neutralizer. The tubes were mixed thoroughly. After 2 minutes, the neutralized suspension was serially diluted 1:10, in physiological saline solution in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9.1 ml of neutralizer and 1 ml of disinfectant with 100 µl of the $1{:}1\times10^6$ dilution of the titer. This produced about 130 CFU/ml in the tube, which was allowed to stand for 20 minutes prior to dilution and assay by membrane filtration using duplicate 1 ml samples.

The results are provided as follows:

TABLE 23a

| *Bacillus Subtilis* Titer | | | |
|---|---|---|---|
| | Dilution | | |
| | $1{:}1\times10^7$ | $1{:}1\times10^8$ | $1{:}1\times10^9$ |
| Number of Colonies | TNC* | 106 | 10 |
| | TNC | 115 | 15 |

*TNC—Too Numerous to Count

TABLE 23b

| Disinfectant solution (Example 5) Dilution of *B. subtilis* spores/disinfectant suspension | | | |
|---|---|---|---|
| | Dilution | | |
| | $1{:}1\times10^2$ | $1{:}1\times10^3$ | $1{:}1\times10^4$ |
| 30 Seconds | 0 | 0 | 0 |
| | 0 | 0 | 0 |

TABLE 23c

| Neutralization control Undiluted |
|---|
| 135 |
| 118 |

TABLE 23d

| Sterility Controls | | | |
|---|---|---|---|
| Material | Counts | Material | Counts |
| PSS | 0 | Example 5 | 0 |
| Neutralizer | 0 | Example 7 | 0 |
| Columbia Agar | 0 | — | — |

Results of the titer showed a viable *B. subtilis* spore concentration of $1.11\times10^{10}$ spores per ml in the original suspension. Inoculation of 9.9 ml of disinfectant with 100 µl of this suspension produced an initial concentration of $1.11\times10^8$ spores per ml in the assay tube. Results from these procedures allowed log reduction (LR) and percent kill (PK) values to be calculated using the formulas: 1) $LR=-\text{Log}(S/So)$ where S=concentration of viable organisms after specified contact time, and So=the initial concentration of viable organisms at time zero; and 2) $PK=(1-(S/So))\times100$. These values are shown below in Table 24.

TABLE 24

| Results | | | |
|---|---|---|---|
| Solution | Contact Time | Log Reduction (LR) | Percent Kill (PK) |
| Example 5 | 30 seconds | >7.05 | >99.999991 |
| Example 7 | 30 seconds | >7.05 | >99.999991 |

Neutralization control data revealed that the neutralizer was able to adequately neutralize this disinfectant. Observed counts were consistently higher than those expected. Each of the test disinfectant solutions (Examples 5 and 7) had rapid and potent sporicidal activity. Specifically, each of Examples 5 and 7 was able to achieve greater than 7-log reduction within 30 seconds. As a control, the same culture was tested using the same concentration of peracetic acid with none of the other active ingredients (i.e. without the alcohol or silver content). The compositions of Examples 5 and 7 exhibited a greater kill level by several orders of magnitude.

Example 14

Kill-Time Studies of Sporicidal Activity Using 2.4% Alkaline Glutaraldehyde Disinfectant For comparison purposes, a study was conducted to determine the antimicrobial activity of a 2.4% alkaline glutaraldehyde disinfectant on bacterial endospores from the test organism *Bacillus subtilis*. Glutaraldehyde disinfectant solution is a common disinfectant used in hospitals to kill bacteria and other pathogens that might otherwise be difficult to kill. This study was carried out by performing a standard kill-time suspension test using a suspension of *B. subtilis* endospores. A 15 minute contact time was evaluated.

A test suspension containing endospores from *Bacillus subtilis* (ATCC # 19659) was prepared from a culture grown on Nutrient agar, to which additional sporulation enhancements were added. Plates were harvested with sterile water and endospores were purified by repeated centrifugations and resuspensions in water. The final wash was in 70 wt % ethanol for 30 minutes, to ensure the death of all vegetative bacteria. The spores were resuspended in water containing 0.1 wt % Tween 80 to prevent clumping and stored at 4° C. until used.

A neutralizer was prepared that consisted of 1 ml of freshly made, filter-sterilized sodium bisulfite solution at 5.28 wt %.

The "kill time" procedure was as follows: A 9.9 ml aliquot of the disinfectant was placed in a sterile glass culture tube. The tube was equilibrated in a 20° C. water bath. The tube of disinfectant, 9 ml of 2.4 wt % alkaline glutaraldehyde (Freshly activated CIDEXPLUS, 3.4%, Lot #:2002247TP—diluted to 2.4 wt % with sterile water), was inoculated with 100 μl of the test organism suspension at time zero. After 15 min, 1 ml of spore/disinfectant suspension was removed to 9 ml of neutralizer. The tube was mixed thoroughly. After 2 minutes, the neutralized suspension was serially diluted (1:1×10, 1:1×$10^2$, 1:1×$10^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension.

A neutralizer control was performed by inoculating a mixture of 1 ml of neutralizer and 1 ml of disinfectant with 100 μl of the 1:1×$10^5$ dilution of the titer. This produced about 450 CFU/ml in the tube, which was allowed to stand for 20 minutes prior to dilution and assay by membrane filtration using duplicate 1 ml samples.

The results are provided as follows:

TABLE 27a

| Titer | | | |
|---|---|---|---|
| | Dilution | | |
| | 1:1 × $10^6$ | 1:1 × $10^7$ | 1:1 × $10^8$ |
| Number of Colonies | TNC* | 96 | 0 |
| | TNC | 93 | 0 |

*TNC—Too Numerous to Count

TABLE 27b

| Disinfectant solution (2.4 wt % alkaline glutaraldehyde disinfectant) Dilution of *B. subtilis* spores/disinfectant suspension | | | | |
|---|---|---|---|---|
| | Dilution | | | |
| | 1:1 × $10^1$ | 1:1 × $10^2$ | 1:1 × $10^3$ | 1:1 × $10^4$ |
| 15 minutes | TNC | TNC | TNC | 259 |
| | TNC | TNC | TNC | 52 |

TABLE 27C

| Neutralization control | | |
|---|---|---|
| | Dilution | |
| | 1:1 × $10^1$ | 1:1 × $10^2$ |
| 15 Seconds | 72 | 1 |
| | 70 | 4 |

Sterilization controls indicated zero growth for the glutaraldehyde, sodium bisulfite, water, PSS, and Columbia agar. Results of the titer showed a viable *B. subtilis* spore concentration of 9.45×$10^8$ spores per ml in the original suspension. Inoculation of 9.9 ml of disinfectant with 100 μl of this suspension produced an initial concentration of 9.45×$10^6$ spores per ml in the assay tube. Results from these procedures allowed log reduction (LR) and percent kill (PK) values to be calculated using the formulas: 1) LR=−Log(S/So) where S=concentration of viable organisms after 1 hour, and So=the initial concentration of viable organisms at time zero; and 2) PK=(1−(S/So))×100. These values are shown below in Table 26.

TABLE 28

| Results | | | |
|---|---|---|---|
| Solution | Contact Time | Log Reduction (LR) | Percent Kill (PK) |
| Alkaline glutaraldehyde | 15 min | 0.48 | 67.1 |

Neutralization control data revealed that the neutralizer was able to adequately neutralize this disinfectant. Observed counts were greater than those expected. The 2.4 wt % alkaline glutaraldehyde solution tested had relatively slow sporicidal activity, producing only a 0.48 log-reduction in 15 minutes, which is significantly lower than that produced by any of the exemplary compositions above prepared in accordance with embodiments of the present invention.

Example 15

Kill-Time Studies of *Mycobacterium bovis* Using Lysol® Spray

For comparison purposes, a study was conducted to determine tuberculocidal activity of a Lysol® spray disinfectant (Lysol Spray, spring waterfall scent Lot # B4194-NJ2 1413-A3) on a hard surface using the CRA Environmental Wipe Method. This method is fully described in: Christensen, R. P., R. A. Robison, D. F. Robinson, B. J. Ploeger, R. W. Leavitt, and H. L. bodily, Antimicrobial Activity of Environmental Surface Disinfecants in the Absence and Presence of Bioburden. Journal of the American Dental Association, 119:493-505. 1989.

Specifically, a test suspension containing Mycobacterium bovis (ATCC # 35743) was prepared from a frozen suspension of a standardized culture grown in modified Proskauer-Beck medium. The suspension was thawed and mixed with an equal volume of phosphate-buffered gelatin solution in a Teflon-on-glass tissue grinder on ice. The suspension was homogenized for two minutes, then diluted 1:4 in physiological saline solution (PSS) containing 0.1% Tween 80. The suspension was vortexed and held on ice until used in inoculate the test surface.

A neutralizer mixture consisted of 50 ml flasks of Tryptic soy broth containing 1.0% Tween 80, 1.0% lecithin, and 50 μl of concentrated catalase solution (Sigma, C100, 42,300 units/mg).

The CRA environmental Wipe Method which was used is detailed below. An 8×12 inch piece of laminated plastic counter covering was secured to polypropylene dental trays (size B, Zirc Dental) with silicone adhesive. Lids and trays were sterilized by a hydrogen peroxide gas plasma sterilizer. Two ml of test organism suspension was applied to the surface with a sterile 2×2-in cotton-filled gauze sponge. The surface was allowed to dry 20-30 minutes in a biosafety cabinet under laminar flow. Then 3.5 ml of disinfectant (or water) was applied to a sterile gauze sponge, which was used to wipe the inoculated test surface for 10 seconds using about 150-g pressure with overlapping strokes (20 left to right, followed by 20 top to bottom). After 3 minutes, the trays were flooded with 50 ml of neutralizer and scrubbed for 1 minute with a sterile polypropylene brush to remove and suspend organisms. The fluid was collected and serially diluted 1:10 in physiological saline solution (PSS). The number of viable organisms in selected dilution tubes was assayed by membrane filtration. One ml aliquots were plated in duplicate. The membranes were washed with about 100 ml of sterile PSS and removed to Mycobacteria 7H11 agar plates. The plates were incubated at 37° C. for about three weeks. The number of colonies on each was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 μl of the 1:$10^3$ dilution of the titer containing 1750 CFU. This produced 175 CFU/ml in the tube, which was allowed to stand for 20 minutes prior to dilution and assay of the tubes by membrane filtration using duplicate 1 ml samples.

The results are provided as follows:

TABLE 17a

| Titer | | | |
|---|---|---|---|
| | Dilution | | |
| | 1:1 × $10^3$ | 1:1 × $10^4$ | 1:1 × $10^5$ |
| Number of Colonies | TNC* | TNC | 175 |
| | TNC | TNC | 174 |

*TNC—Too Numerous to Count

TABLE 173b

| Disinfectant solution (Lysol ® Spray) Dilution of *M. bovis*/disinfectant suspension | | |
|---|---|---|
| | Dilution | |
| | Undiluted | 1:1 × $10^1$ |
| 3 minutes | TNC | 640 |
| | TNC | 486 |

TABLE 17c

| Neutralization control Undiluted |
|---|
| 180 |
| 196 |

TABLE 17d

| Sterility controls | |
|---|---|
| Material | Counts |
| Phosphate buffered gelatin | 0 |
| Neutralizer + catalas | 0 |
| Lysol Spray | 0 |
| Mycobacteria 7H11 Agar | 0 |
| Physiological sterile saline (PSS) + 0.1% Tween 80 | 0 |
| Physiological sterile saline (PSS) | 0 |

Results of the titer showed the initial concentration of *M. bovis* was 1.75×107 CFU per ml in the prepared suspension. Innoculation of the test surface following drying proceduced a challenge exhibited by the water control. The initial concentration of viable bacilli on the test surface (So) was 2.63×$10^5$. Results from these procedures allowed log reduction (LR) and percent kill (PK) 15 values to be calculated using the formulas: 1) LR=−Log(S/So) where S=Concentration of viable organisms after a period of exposure to the disinfectant; and So=the initial concentration of viable organisms at time zero; These values are shown in the Table 18 below.

TABLE 18

| Results | | | |
|---|---|---|---|
| Solution | Contact Time | Log Reduction (LR) | Percent Kill (PK) |
| Lysol ® Spray | 3 minutes | 0.97 | 89.3 |

The neutralization control data indicated that each test solution was adequately neutralized. Observed counts were similar to those expected from the titer data.

Example 16

Kill-Rate Enhancement Using Certain Alloys

To demonstrate the effectiveness of certain alloys in enhancing the kill rate of *B. Subtilis* bacteria, a composition comprising 0.5% by weight of hydrogen peroxide, 8% by weight ethanol, and the balance of water containing 300 ppm of a colloidal silver was prepared. A similar composition was prepared using identical components except that aqueous solution contained a silver alloy admixture with manganese (approximately 300 ppm silver and about 7 ppm manganese). A kill test was performed resulting in a 0.13 log reduction or a 25.6% kill rate of the *B. subtilis* after 30 seconds using the colloidal silver composition. The kill study was also performed using the colloidal silver-manganese alloy composition, which resulted in a 0.24 log reduction or 42.6% kill after 30 seconds.

Example 17

Disinfectant Mouthwash

A disinfectant mouthwash (oral rinse) is made using the disinfectant composition described in one of Examples 1 to 9. The mouthwash is made by combining the disinfectant composition with sorbitol (sweetener), sodium fluoride (fluoride ion component) in an amount sufficient to provide 250 ppm of the fluoride ion, and mint oil (flavoring). The ingredients are mixed with the disinfectant composition of one of the Examples diluted by about 1:10 by weight with water. It is noted that by diluting the total composition at a 1:10 by weight with water, the colloidal silver content is significantly reduced. If the desire is to have higher weight percentages of colloidal silver, the silver content can be formulated to be higher than that in Examples 1 to 9, so that when the mouthwash is diluted, a higher silver content will be present in the solution.

Example 18

Disinfectant Toothpaste

A disinfectant toothpaste is made using the disinfectant composition of one of Examples 1 to 9. The toothpaste is made by mixing the disinfectant composition with the water, hydrated silica, sorbitol, glycerin, sodium lauryl sulfate, titanium dioxide, menthol, pentasodium triphosphate, and PEG-6. The ingredients are mixed together in amounts sufficient to yield a paste with disinfectant properties. Again, it is noted that by diluting the total composition with paste-forming and other ingredients, the ionic silver content is significantly reduced. If the desire is to have higher weight percentages of silver, the silver content can be formulated to be higher than that in the composition examples above, so that when the toothpaste is formulated, a higher silver content will be present in the paste.

Example 19

Disinfectant Ointment

A disinfectant ointment is prepared using the disinfectant solution of one of Example 1 to 9. The disinfectant is mixed with aloe vera gel forming a disinfectant ointment. The gel is then applied to an infection on the skin of a subject. The disinfectant ointment disinfects the skin and provides some relief from the irritation of the infection.

Example 20

Disinfectant Soap or Shampoo

A disinfectant liquid soap is prepared using the disinfectant solution of one of Examples 1 to 9. The disinfectant is mixed with water, sodium laureth sulfate, sodium lauryl sulfate, sodium sulfate, cocamidopropyl betaine, citric acid, sodium chloride, fragrance, DMDM hydantoin, and tetrasodium EDTA yielding a disinfectant liquid soap or shampoo. The soap or shampoo has a viscosity allowing it to be readily dispensed using traditional pump dispensers. Hard hand soaps can similarly be prepared by using the disinfectant as one of the ingredients for use in the soap forming process.

Example 21

Disinfectant Wipe

A disinfectant wipe is prepared using the disinfectant solution of one of Examples 1 to 9. A nonwoven cotton fabric is impregnated with the disinfectant solution. The wipes are prepared by placing a stack cotton fabric sheets in a container, saturating the fabric sheets with the disinfectant solution, and placing a cover over the container and sealing the container against evaporation of the disinfectant solution. If the disinfectant solution includes colloidal metal, care is taken to make sure that each and every piece of nonwoven cotton fabric is exposed to not only the liquid, but to the solid particles as well.

Example 22

Disinfectant Gel

A disinfectant gel is prepared using the disinfectant solution of one of Examples 1 to 9. The disinfectant is mixed with aloe vera gel forming a disinfectant gel. The gel is then applied to an infection on the skin of a subject. The disinfectant gel disinfects the skin and provides some relief from the irritation of the infection.

Example 23

Disinfectant Aerosol and/or or Fog

The disinfectant composition of one of Examples 1 to 9 is used to form a disinfectant fog. Using a thermal fogger from Dyno-Fog® the disinfectant composition is aerosolized into small droplets in a room in need of sterilization, e.g., a hospital room. The disinfectant fog is allowed to fill the room. The disinfectant fog sterilizes and disinfects the air and the hard surfaces in the room. After a period of about 40 minutes, the aerosolized particles are substantially settled out of the air and the room is substantially disinfected.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. An aqueous disinfectant composition, comprising:

a) an aqueous vehicle, including:

i) water;

ii) from 0.001 wt % to 10.0 wt % of a peroxygen, said peroxygen including a metal peroxide, iii) an alcohol; and b) from 0.001 ppm to 50,000 ppm by weight of a transition metal or alloy thereof based on the aqueous vehicle content.

2. A composition as in claim 1, wherein the metal peroxide is selected from the group consisting of sodium peroxide, magnesium peroxide, calcium peroxide, barium peroxide, and strontium peroxide, and mixtures thereof.

3. An aqueous disinfectant composition, comprising:

a) an aqueous vehicle, including:

i) water;

ii) from 0.001 wt % to 10.0 wt % of a peroxygen, said peroxygen including a peroxyhydrate;

iii) an alcohol; and b) from 0.001 ppm to 50,000 ppm by weight of a transition metal or alloy thereof based on the aqueous vehicle content.

4. An aqueous disinfectant composition, comprising:

a) an aqueous vehicle, including:

i) water;

ii) from 0.001 wt % to 10.0 wt % of a peroxygen, said peroxygen including a peroxide generated in situ;

iii) an alcohol; and b) from 0.001 ppm to 50,000 ppm by weight of a transition metal or alloy thereof based on the aqueous vehicle content.

5. A composition as in claim 4, wherein the peroxide generated in situ is hydrogen peroxide generated from sodium percarbonate.

6. An aqueous disinfectant composition, comprising:

a) an aqueous vehicle, including:

i) water;

ii) from 0.001 wt % to 10.0 wt % of a peroxygen, wherein the peroxygen includes a peracid; and iii) an alcohol;

b) from 0.001 ppm to 50,000 ppm by weight of a colloidal transition metal or alloy thereof based on the aqueous vehicle content.

7. A composition as in claim 6, wherein the disinfectant composition is substantially free of chlorine and bromine-containing components.

8. A composition as in claim 6, wherein the disinfectant composition is substantially free of iodophore-containing components.

9. A composition as in claim 6, wherein the disinfectant composition is substantially free of phenolic-containing components.

10. A composition as in claim 6, wherein the disinfectant composition is substantially free of quaternary ammonium-containing components.

11. A composition as in claim 6, where the alcohol is present at from 0.001 wt % to 40 wt %.

12. A composition as in claim 6, wherein the alcohol is present at from 0.05 wt % to 20 wt %.

13. A composition as in claim 6, wherein the alcohol is present at from 0.1 wt % to 10 wt %.

14. A composition as in claim 6, wherein the alcohol is a $C_1$-$C_{24}$ alcohol.

15. A composition as in claim 14, wherein $C_1$-$C_{24}$ alcohol is selected from the group consisting of methanol, ethanol, propanols, butanols, pentanols, and mixtures thereof.

16. A composition as in claim 14, wherein the $C_1$-$C_{24}$ alcohol is a polyhydric alcohol.

17. A composition as in claim 16, wherein the polyhydric alcohol is glycerol.

18. A composition as in claim 16, wherein the polyhydric alcohol includes two alcohol groups.

19. A composition as in claim 16, wherein the polyhydric alcohol includes three alcohol groups.

20. A composition as in claim 6, wherein the transition metal or alloy thereof is a Group VI to Group XI transition metal or alloy thereof.

21. A composition as in claim 6, wherein the transition metal or alloy thereof is a Group X to Group XI transition metal or alloy thereof.

22. A composition as in claim 6, wherein the transition metal or alloy thereof is selected from the group consisting of ruthenium, rhodium, osmium, iridium, palladium, platinum, copper, gold, silver, alloys thereof, or mixtures thereof.

23. A composition as in claim 22, wherein the colloidal transition metal is colloidal silver.

24. A composition as in claim 22, wherein the colloidal transition metal or alloy thereof has an average particle size of from 0.001 μm to 1.0 μm.

25. A composition as in claim 22, wherein the colloidal transition metal or alloy thereof has an average particle size of from 0.03 μm to 0.5 μm.

26. A composition as in claim 6, wherein the transition metal or alloy thereof is present at from 15 ppm to 1500 ppm by weight.

27. A composition as in claim 6, wherein the peracid is an aliphatic peracid.

28. A composition as in claim 6, wherein the peracid is an aromatic peracid.

29. A composition as in claim 6, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

30. A composition as in claim 6, wherein the peroxygen is present at from 0.05 wt % to 5.0 wt % as part of the aqueous vehicle.

31. A composition as in claim 6, wherein the peroxygen is present at from 0.1 wt % to 3.0 wt % as part of the aqueous vehicle.

32. A composition as in claim 6, wherein the peroxygen is present at from 0.1 wt % to 1.5 wt % as part of the aqueous vehicle.

33. A composition as in claim 6, wherein the peroxygen includes a peroxide.

34. A composition as in claim 33, wherein the peroxide is hydrogen peroxide.

35. A composition as in claim 33, wherein the peroxide is a metal peroxide.

36. A composition as in claim 35, wherein the metal peroxide is selected from the group consisting of sodium peroxide, magnesium peroxide, calcium peroxide, barium peroxide, and strontium peroxide, and mixtures thereof.

37. A composition as in claim 33, wherein the peroxide is a peroxyhydrate.

38. A composition as in claim 33, wherein the peroxide is generated in situ.

39. A composition as in claim 38, wherein the peroxide is hydrogen peroxide generated from sodium percarbonate.

40. A composition as in claim 6, wherein the peroxygen includes a peracid and a peroxide.

41. A composition as in claim 6, wherein the peroxygen is a peracid salt.

42. A composition as in claim 41, wherein the peracid salt is selected from the group consisting of permanganates, perborates, perchlorates, peracetates, percarbonates, persulphates, and combinations thereof.

43. A composition as in claim 6 impregnated in a fabric as a disinfectant wipe.

44. A composition as in claim 6, further comprising a thickening or gelling agent having the aqueous composition admixed therein to form a disinfectant gel.

45. A composition as in claim 6, in the form of an aerosolized disinfectant having a particle size from about 5 μm to about 200 μm.

46. A composition as in claim 6, further comprising a foaming agent to form a disinfectant foam.

47. A composition as in claim 6, formulated in a personal hygiene product selected from the group consisting of a shampoo, a soap, a gel, a cream or ointment, a toothpaste, or an oral rinse.

48. An aqueous disinfectant composition, comprising:

a) an aqueous vehicle, including:
   i) water;
   ii) from 0.001 wt % to 10.0 wt % of a peroxygen, wherein the peroxygen includes a peracid; and
   iii) an alcohol;
b) from 0.001 ppm to 50,000 ppm by weight of a colloidal silver or alloy thereof based on the aqueous vehicle content.

49. A composition as in claim 48, wherein the disinfectant composition is substantially free of aldehydes, chlorine and bromine-containing components, iodophore-containing components, phenolic-containing components, and quaternary ammonium-containing components.

50. A composition as in claim 48, wherein the alcohol is present at from 0.001 wt % to 40 wt %.

51. A composition as in claim 48, wherein the alcohol is present at from 0.1 wt % to 10 wt %.

52. A composition as in claim 48, wherein the alcohol is a polyhydric alcohol.

53. A composition as in claim 48, wherein the colloidal silver or alloy thereof is an alloy selected from the group consisting of silver, ruthenium, rhodium, osmium, iridium, palladium, platinum, copper, or gold.

54. A composition as in claim 48, wherein the colloidal silver or alloy thereof has an average particle size of from 0.001 μm to 1.0 μm.

55. A composition as in claim 48, wherein the transition metal or alloy thereof is present at from 15 ppm to 1500 ppm by weight.

56. A composition as in claim 48, wherein the peracid is an aliphatic peracid or an aromatic peracid.

57. A composition as in claim 48, wherein the peroxygen is present at from 0.05 wt % to 5.0 wt % as part of the aqueous vehicle.

58. A composition as in claim 48, impregnated in a fabric as a disinfectant wipe.

59. A composition as in claim 48, further comprising a thickening or gelling agent having the aqueous composition admixed therein to form a disinfectant gel.

60. A composition as in claim 48, in the form of an aerosolized disinfectant having a particle size from about 5 μm to about 200 μm.

61. A composition as in claim 48, further comprising a foaming agent to form a disinfectant foam.

62. A composition as in claim 48, formulated in a personal hygiene product selected from the group consisting of a shampoo, a soap, a gel, a cream, an ointment, a toothpaste, or an oral rinse.

63. A method of disinfecting a surface, comprising: contacting the surface with a disinfectant composition, comprising:

a) an aqueous vehicle, including:
   i) water;
   ii) from 0.001 wt % to 10.0 wt % of a peroxygen, wherein the peroxygen includes a peracid; and
   iii) an alcohol;
b) from 0.001 ppm to 50,000 ppm by weight of a colloidal transition metal or alloy thereof based on the aqueous vehicle content.

64. A method as in claim 63, wherein the alcohol is present at from 0.05 wt % to 40 wt %.

65. A method as in claim 64, wherein the alcohol is present at from 0.1 wt % to 10 wt %.

66. A method as in claim 63, wherein the alcohol is a $C_1$-$C_{24}$ alcohol and is selected from the group consisting of methanol, ethanol, propanols, butanols, pentanols, or mixtures thereof.

67. A method as in claim 63, wherein the $C_1$-$C_{24}$ alcohol is a polyhydric alcohol.

68. A method as in claim 63, wherein the polyhydric alcohol is glycerol.

69. A method as in claim 63, wherein the transition metal or alloy thereof is a Group VI to Group XI transition metal or alloy selected from the group consisting of ruthenium, rhodium, osmium, iridium, palladium, platinum, copper, gold, silver, alloys thereof, or mixtures thereof.

70. A method as in claim 63, wherein the colloidal transition metal is colloidal silver.

71. A method as in claim 63, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

72. A method as in claim 63, wherein the peroxygen is present at from 0.05 wt % to 5.0 wt % as part of the aqueous vehicle.

73. A method as in claim 63, wherein the peroxygen is present at from 0.1 wt % to 3.0 wt % as part of the aqueous vehicle.

74. A method as in claim 63, wherein the peroxygen is present at from 0.1 wt % to 1.5 wt % as part of the aqueous vehicle.

75. A method as in claim 63, wherein the peroxygen includes a peroxide.

76. A method as in claim 75, wherein the peroxide is selected from the group consisting of hydrogen peroxide, sodium peroxide, magnesium peroxide, calcium peroxide, barium peroxide, and strontium peroxide, or mixtures thereof.

77. A method as in claim 63, wherein the peroxygen includes a peracid and a peroxide.

78. A method as in claim 63, wherein the peroxygen is a peracid salt selected from the group consisting of permanganates, perborates, perchlorates, peracetates, percarbonates, persulphates, and combinations thereof.

* * * * *